United States Patent [19]

Matsushita

[11] 4,098,575
[45] Jul. 4, 1978

[54] PEROXIDE VALUE DETERMINING TEST FOR OILS AND FATS

[75] Inventor: Setsuro Matsushita, Kyoto, Japan

[73] Assignee: Zaidan-hoijin Sugiyama Sangyo Kagaku Kenkyusho, Yokohama, Japan

[21] Appl. No.: 676,630

[22] Filed: Apr. 13, 1976

[30] Foreign Application Priority Data

Jun. 19, 1975 [JP] Japan ................... 50-75309

[51] Int. Cl.$^2$ ..................... G01N 31/22; G01N 33/02
[52] U.S. Cl. ............................ 23/230 R; 23/253 TP
[58] Field of Search ................ 23/230 R, 253 TP, 231

[56] References Cited

U.S. PATENT DOCUMENTS

| 3,183,173 | 5/1965 | Oakes | 23/253 TP X |
|---|---|---|---|
| 3,705,012 | 12/1972 | Marmor et al. | 23/230 R |
| 3,826,620 | 7/1974 | Simpson et al. | 23/253 TP |
| 3,846,247 | 11/1974 | Kronish et al. | 23/253 TP X |
| 3,897,214 | 7/1975 | Lange et al. | 23/253 TP |
| 3,901,657 | 8/1975 | Lightfoot | 23/253 TP |
| 3,937,613 | 2/1976 | Rosicky | 23/253 TP |

FOREIGN PATENT DOCUMENTS

| 264,474 | 8/1964 | Australia | 23/253 TP |
|---|---|---|---|
| 125,817 | 1/1968 | Czechoslovakia | 23/253 TP |

*Primary Examiner*—Morris O. Wolk
*Assistant Examiner*—Arnold Turk
*Attorney, Agent, or Firm*—Browdy and Neimark

[57] ABSTRACT

A test paper, manufactured by impregnating a glass fiber-made paper or cloth with a starch and potassium iodide reagent, liberates iodine on the test paper in such a quantity as to exactly correspond to the peroxide content of an oil or fat coming into contact therewith. Since the liberated iodine easily combines with the ambient starch and turns blue in accordance with the quantity of iodine upon subsequent addition of water, determination of the peroxide value, or consequently the edibility, of the oil or fat can be conveniently effected by determinaton of merely finding the intensity of the color developed on the test paper.

7 Claims, 2 Drawing Figures

PEROXIDE VALUE DETERMINING TEST FOR OILS AND FATS

FIELD OF THE INVENTION

The present invention relates to a test paper to enable the convenient determination of the peroxide values of an oil, etc. said test paper being index for the degree of oxidation or deterioration thereof, being manufactured by impregnating a glass fibre-made paper or cloth with a starch and potassium iodide reagent solution and, after that, drying.

BACKGROUND OF THE INVENTION

Oils or fats including edible oil are in great demand every day as the principal materials for foods, cooking and so forth, therefore, a determination of the degree of oxidation or deterioration of oils or fats is a daily requirement from the viewpoint of hygiene and sanitation, tastes and odors of foods manufactured or cooked, or the like.

When an oil or fat is oxidized or deteriorated, it generally is accompanied by an unpleasant odor. So, the degree of oxidation or deterioration of an oil or fat may be, to some extent, judged by smelling. However, such judgement requires skills and besides is never expected to be accurate. For a judgement of the degree of oxidation or deterioration of an oil or fat, determination of peroxide value, carbonyl value, acid value, TBA value (to be determined by adding 2-thiobarbituric acid to a sample oil or fat, heating the mixture, removing the oil layer with the aid of chloroform, determining the absorbance at 532 m$\mu$ of the aqeous layer, and calculating the milligrams of malonic aldehyde equivalent to the absorbance per 1 kg of the sample oil or fat), etc. is usually conducted, and other than this no proper judging method is to be found today.

However, operations for such determination of the values need some technical skills as well as experimental apparatus, and moreover they are rather troublesome for ordinary people, and accordingly the determining operations are not compatible with usual kitchen or factory works.

SUMMARY OF THE INVENTION

The present invention has been made in an attempt to facilitate these determining operations and to enable them to be conducted easily even in a kitchen or factory. In accordance with the present invention, a convenient test paper is provided, which enables people to readily carry out a determination of the peroxide value of an oil or fat without any technical skills or knowledge. The test paper comprises a glass fiber-made paper or cloth impregnated with a starch and potassium iodide reagent solution which is then dried.

BRIEF DESCRIPTION OF THE DRAWINGS

The present invention will be understood and its several advantages appreciated from the detailed description which follows, read in connection with the accompanying drawings showing:

A perspective view of an embodiment of the present invention in FIG. 1 and

Figure 2:
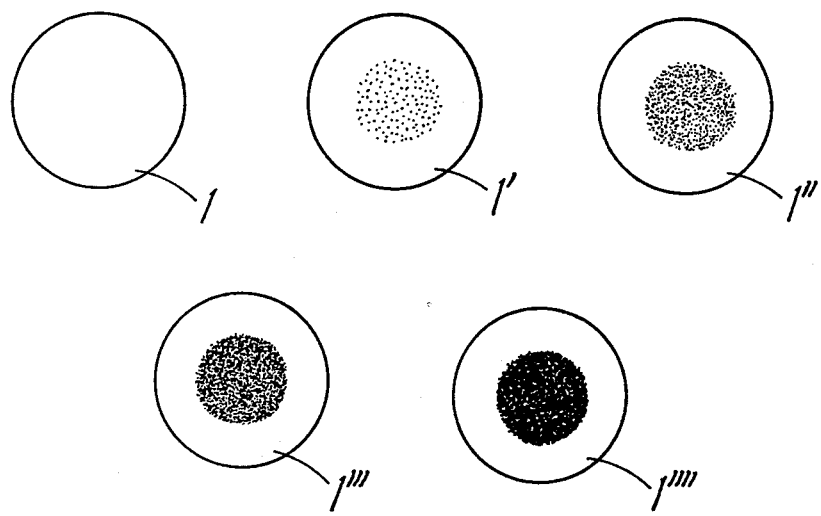

An illustration showing the results of the use thereof in FIG. 2.

DESCRIPTION OF PREFERRED EMBODIMENTS

In case an oil or fat is autoxidized, hydroperoxide is produced as the primarily stable product. When the peroxide reacts with potassium iodide, iodine is liberated which is to be titrated with a thiosulfate solution, and the peroxide value of a sample oil or fat is shown by the milliequivalents of the iodine per 1 kg of the sample oil or fat (vide The Standard Analytical and Testing Method for Oils and Fats, 1972 year Edition by The Oil Chemical Society of Japan).

The present invention has been made as the result of work done in order to have the peroxide value determining process conducted on a test paper and to produce easy and convenient means for its determination. The present invention has enabled the peroxide value of an oil or fat to be precisely determined by the color developed on a test paper, and it is based on the finding that a test paper, manufactured by impregnating a glass fiber-made paper or cloth with a starch and potassium iodide reagent solution and then drying, sensitively reacts with the peroxide component in an oil or fat added to it and liberates iodine in such quantity as to be proportional in a straight line relation to the peroxide content of the oil or fat, and further the iodine liberated colors the ambient starch blue upon subsequent addition of water, and accordingly the intensity of the blue color developed on the test paper is proportional in a straight line relationship to the peroxide value of the oil or fat.

The above test paper relating to the present invention may fall in the category of the so-called starch and potassium iodide test papers. However, those test papers available on the market for the use of detection of hypochlorite, etc. as obtainable by impregnating or coating filter papers of vegetable fiber nature or the like with a starch and potassium iodide reagent solution, those test papers as manufactured by impregnating papers or cloths of a synthetic or chemical fiber nature with the same reagent solution, or the like can liberate no or a very insufficient quantity of iodine at the time they come into contact with an oxidized or deteriorated oil or fat. Therefore, they can be of no or hardly any use as the test paper for the purpose of the present invention.

The peroxide value determining test paper of the present invention is constituted of a glass fiber-made paper or cloth which is impregnated with a starch and potassium iodide reagent solution and thereafter dried. Such glass fiber-made paper or cloth for the test paper can be readily prepared by cutting, etc. out of a glass fiber-made filter paper or filter cloth of the like. The starch and potassium iodide reagent solution also can be prepared readily in the same manner as for the usual reagent solution; however, a reagent solution about two times as concentrated as usual, with respect to the potassium iodide ingredient, is preferable for the purpose of the present invention from the point of view of facilitating the distinguishing of the colors developed.

The present invention will be more clearly understood with reference to the following embodiments; however, they are intended to explain in detail the invention and are not construed to limit the scope of the invention.

Figure 1:
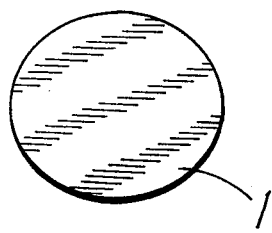

To 100 ml of water is added 1 g of soluble starch, and the mixture is heated and brought to a clear solution. After the solution is allowed to cool, 0.5 g of potassium iodide is added to it. Then discs of about one inch in diameter, each of which is made by cutting out of a Watman glass fiber-made filter paper, GF/A, are steeped in the solution and are well impregnated therewith. After that, the discs are taken out of the solution and dried in a clean and dry air. Thus, the disc-like peroxide value determining test papers for oils and fats 1, as shown in FIG. 1 of the accompanying drawings, are obtained.

An example of the application of the above prepared test papers 1 for determination of peroxide values of oils and the result of the application are as given below.

One drop each of five kinds of edible oils, the peroxide values of which are precisely determined beforehand by the normal titration method and found to be 5, 30, 50, 100 and 200 respectively, is put on the above prepared disc-like test papers, 1, 1', 1'', 1''' and 1''''. One minute later, iodine in such quantity as proportional to the peroxide value of each oil is liberated on the respective test papers. Then, two or three drops of water are put on the respective test papers, and, in a few minutes, blue colors, due to the iodide of starch are produced at the parts of the liberated iodine on the test papers, with such distinct differences in shade as shown in FIG. 2 of the accompanying drawings.

Judgment for edibility of an oil or fat, on the basis of its peroxide value, is usually made as to whether the value falls within the limit of about 30 or not. So, in case of the test papers used for the above application example, an oil or fat or the like which are destined to develop colors less than very slightly blue on the test papers, just as shown on 1' of FIG. 2, will be immediately judged to be edible so far as concerned with peroxide value.

Incidentally, by taking into consideration the above mentioned TBA value together with the peroxide value, oxidation or deterioration degree of an oil or fat will almost completely be made clear.

Another embodiment of the present invention is as follows:

To 100 ml of water is added 2 g of soluble starch, and the mixture is heated and brought to a clear solution. After the solution is allowed to cool, 0.5 g of potassium iodide, 0.01 g of ascorbic acid as a reducing agent and 0.02 g of citric acid (as hydrate) are added to it. Then, peroxide value determining test papers are manufactured in the same way as in the foregoing embodiment, using the solution and Watman glass fiber-made filter paper. For the above reducing agent, sodium sulfite, cysteine hydrochloride, etc. are also usable in place of the ascorbic acid.

The addition of a small amount of reducing agent is useful in protecting the glass fiber-made paper or cloth with the reagent from possible yellowing at the time of the drying thereof, and the addition of a small amount of citric acid is advantageous for making the resultant blue color on the test paper somewhat clearer.

In case of a solid fat, peroxide value determining with use of the test paper relating to the present invention shall, as a matter of course, be carried out at temperatures above the melting point of the fat. Even in this case also, the test paper undergoes no change in its coloring nature and is usable in the same way as in the case for a liquid oil, except for the temperature.

As obvious according to the above, the test paper relating to the present invention, manufactured by impregnating a glass fiber-made paper or cloth with a starch and potassium iodide reagent solution and then drying, works excellently to sensitively liberate iodine in such a quantity as to be proportional in a straight line relationship to the peroxide value of an oil or fat in contact therewith, and further results in the iodine coloring the ambient starch in shades proportional in a straight line relationship to the peroxide value of the oil or fat upon subsequent contact with water.

In this way, the test paper relating to the present invention enables people to determine the peroxide value of an oil or fat, or, consequently, to judge the edibility thereof, very readily with the simple operation of putting on the test paper one drop of the oil or fat and later a few drops of water. Therefore, the present invention will produce a very useful and advantageous means to those handling oils and fats, including the production or storage thereof, application thereof to foods manufactured or cooked and so forth.

What I claim is:

1. A method for determining the peroxide value of oils and fats, comprising:
   placing a predetermined amount of oil or fat on a glass fiber-made paper or cloth impregnated with a starch and potassium iodide reagent solution which has subsequently been dried;
   placing a predetermined amount of water on said paper or cloth on which the oil or fat has been placed; and
   comparing the color on said paper or cloth to a predetermined standard.

2. A method as defined in claim 1 wherein said starch and potassium iodide reagent solution includes a small amount of citric acid.

3. A method as defined in claim 1 wherein said starch and potassium iodide reagent solution includes a small amount of a reducing agent.

4. A method as defined in claim 3, wherein said starch and potassium iodide reagent solution includes a small amount of citric acid.

5. A method as defined in claim 1 wherein said glass fiber-made paper or cloth is a glass fiber-made filter paper.

6. A method as defined in claim 5, wherein said starch and potassium iodide reagent solution includes a small amount of a reducing agent.

7. A method as defined in claim 5, wherein said starch and potassium iodide reagent solution includes a small amount of citric acid.

* * * * *